United States Patent
Kim et al.

(10) Patent No.: US 10,379,108 B2
(45) Date of Patent: Aug. 13, 2019

(54) DISTINCTION OF INFECTIOUS VIRUS BASED ON MOLECULAR BIOMARKER AND NEUTRALIZATION OF VIRUS CAUSING FOOD POISONING

(71) Applicants: INDUSTRY FOUNDATION OF CHONNAM NATIONAL UNIVERSITY, Gwangju (KR); KOREA BASIC SCIENCE INSTITUTE, Daejeon (KR)

(72) Inventors: Du Woon Kim, Gwangju (KR); Joseph Kwon, Jeollabuk-do (KR)

(73) Assignees: INDUSTRY FOUNDATION OF CHONNAM NATIONAL UNIVERSITY, Gwangju (KR); KOREA BASIC SCIENCE INSTITUTE, Daejeon (KR)

( * ) Notice: Subject to any disclaimer, the term of this patent is extended or adjusted under 35 U.S.C. 154(b) by 37 days.

(21) Appl. No.: 15/151,180

(22) Filed: May 10, 2016

(65) Prior Publication Data

US 2017/0285011 A1    Oct. 5, 2017

(30) Foreign Application Priority Data

May 11, 2015 (KR) .................. 10-2015-0065567

(51) Int. Cl.
*G01N 33/50* (2006.01)
*C12Q 1/68* (2018.01)
*A61K 38/16* (2006.01)
*G01N 33/569* (2006.01)

(52) U.S. Cl.
CPC ....... *G01N 33/5088* (2013.01); *A61K 38/168* (2013.01); *C12Q 1/68* (2013.01); *G01N 33/5091* (2013.01); *G01N 33/56983* (2013.01); *G01N 2333/08* (2013.01); *G01N 2333/4603* (2013.01); *Y02A 50/463* (2018.01)

(58) Field of Classification Search
CPC ......... G01N 33/5088; G01N 33/56983; G01N 33/5091; G01N 2333/08; G01N 2333/4603; A61K 38/168; C12Q 1/68; Y02A 50/463
See application file for complete search history.

(56) References Cited

U.S. PATENT DOCUMENTS

| | | | |
|---|---|---|---|
| 4,742,046 A | 5/1988 | Bliah | 514/8 |
| 2003/0206923 A1* | 11/2003 | Sun | A61K 36/06 424/195.15 |
| 2007/0218458 A1* | 9/2007 | Tullis | A61L 2/02 435/5 |
| 2011/0144031 A1 | 6/2011 | Lei et al. | 514/19.3 |
| 2014/0128317 A1* | 5/2014 | Lentzen | A61K 38/168 514/4.2 |
| 2016/0090640 A1* | 3/2016 | Kwon | C12Q 1/701 435/5 |
| 2017/0285011 A1* | 10/2017 | Kim | G01N 33/5088 |

FOREIGN PATENT DOCUMENTS

| | | | |
|---|---|---|---|
| KR | 20140126664 A | * 10/2014 | |
| KR | 10-2014-0136250 | 11/2014 | G01N 33/15 |

OTHER PUBLICATIONS

Kim et al. (Biomaterials. 2017; 128: 33-43).*
Levraud et al (Trends in Microbiology. Sep. 2014; 22 (9): 490-497).*
Varela et al. (Antiviral Research. 2017; 139: 59-68).*
Greening, Gail E., and Jennifer L. Cannon. ("Human and animal viruses in food (including taxonomy of enteric viruses)." Viruses in foods. Springer International Publishing, 2016. 5-57.*
Idris et al. (Archives of Virology. 2016; 161: 1751-1760).*
Yang et al. (International Immunology. 2010; 2 (8): 661-670).*
De Graaf et al. (Nature Reviews Microbiology. 2016; 14 (7): 421-433).*
Barton C, Kouokam JC, Lasnik AB, Foreman O, Cambon A, Brock G, Montefiori DC, Vojdani F, McCormick AA, et. al. Activity of and effect of subcutaneous treatment with the broad-spectrum antiviral lectin griffithsin in two laboratory rodent models. Antimicrob Agents Chemother. 2014;58(1):120-7. Epub Oct. 21, 2013.*
Zhu JD, Meng W, Wang XJ, Wang HC. Broad-spectrum antiviral agents. Front Microbiol. May 22, 2015;6:517.*
Hasenack BS, Botelho MVJ, Lauretti FM, Fernando L. de OJM, Linhares REC, Ueda M, Nozawa CM. (2002). The effect of concanavalin A on the replication of rotavirus (SA-11) in cell culture. Brazilian Archives of Biology and Technology, 45(2), 125-135.*
Hong SA, Kwon J, Kim D, Yang S. A rapid, sensitive and selective electrochemical biosensor with concanavalin A for the preemptive detection of norovirus. Biosens Bioelectron. Feb. 15, 2015;64:338-44. Epub Sep. 16, 2014.*
Slifkin M, Doyle RJ. Lectins and their application to clinical microbiology. Clin Microbiol Rev. Jul. 1990;3(3):197-218.*
Tan M, Wei C, Huang P, Fan Q, Quigley C, Xia M, Fang H, Zhang X, Zhong W, Klassen JS, Jiang X. Tulane virus recognizes sialic acids as cellular receptors. Sci Rep. Jul. 6, 2015;5:11784.*
Bok, K., et al., (2010). "Chimpanzees as an animal model for human norovirus infection and vaccine development". www.pnas.org/cgi/doi/10.1073/pnas.1014577107. 108(1):325-330.
Burgos, J., et al., (2008). "Zebrafish as a new model for herpes simplex virus type 1 infection". *HSV-1 Infection in Zebrafish*. 5(4):323-335.
Clackson, T., et al., (1991). "Making antibody fragments using phage display libraries". *Letter to Nature*. 352:624-628.
Ding, C., et al., (2011). "Zebrafish as a potential model organism for drug test against hepatitis c virus". www.plosone.org. 6(8):1-8.

(Continued)

*Primary Examiner* — Rachel B Gill
(74) *Attorney, Agent, or Firm* — Harness, Dickey & Pierce, P.L.C.

(57) ABSTRACT

Discloses are a method for detecting Norovirus using a Norovirus animal model, a method for screening an antivial agent against Norovirus, and a composition for neutralizing the infection with an enteric virus, containing concanavalin A as an active ingredient, so that the method for detecting Norovirus can allow the distinction between infectious Norovirus and non-infectious Norovirus, and the composition can neutralize a virus causing food poisoning.

7 Claims, 15 Drawing Sheets

(56) References Cited

OTHER PUBLICATIONS

Köhler, G., et al, (1976). "Derivation of specific antibody-producing tissue culture and tumor lines by cell fusion". *Eur. J. Immunol.* 6:511-519.

Marks, J., et al., (1991) "By-passing immunization human antibodies from v-gene libraries displayed on phage". *J. Mol. Biol.* 222:581-597.

Palha, N., et al., (2013). "Real-time whole-body visualization of chikungunya virus infection and host interferon response in zebrafish". www.plospathogens.org 9(9):1-15.

Office Action from corresponding Korean Patent Application No. 10-2015-0065567 dated Nov. 16, 2016.

Gabor, K., et al.: "Influenza A virus infection in zebrafish recapitulates mammalian infection and sensitivity to anti-influenza drug treatment", Disease Models & Mechanisms, 2014, vol. 7, pp. 1227-1237.

Vashist, S., et al.: "Molecular Chaperone Hsp90 Is a Therapeutic Target for Noroviruses", Journal of Virology, 2015, vol. 89, No. 12, pp. 6352-6363.

Extended European Search Report from corresponding European Patent Application No. 16170158.6 dated Oct. 27, 2016.

Hasenack, B., et al.: "The Effect of Concanavalin A on the Replication of Rotavirus (SA-11) in Cell Culture", Brazilian Archives of Biology and Technology, 2002, vol. 45, No. 2, pp. 125-135.

Notice of Allowance from corresponding Korean Patent Application No. 10-2017-0007000 dated Jul. 27, 2017.

Notice of Allowance from corresponding Korean Patent Application No. 10-2015-0065567 dated May 23, 2017.

* cited by examiner

M: 100 bp marker
1: *Norovirus* heated at 50°C for 10 minutes
2: *Norovirus* heated at 60°C for 10 minutes
3: *Norovirus* heated at 70°C for 10 minutes
4: *Norovirus* heated at 80°C for 10 minutes
5: *Norovirus* heated at 90°C for 10 minutes

DISTINCTION OF INFECTIOUS VIRUS BASED ON MOLECULAR BIOMARKER AND NEUTRALIZATION OF VIRUS CAUSING FOOD POISONING

CROSS-REFERENCE TO RELATED APPLICATIONS

This application claims the benefit and priority of Korean Patent Application No. 10-2015-0065567, filed 11 May 2015. The entire disclosure of the above application is incorporated herein by references.

FIELD

The present invention relates to a distinction of an infectious virus based on a molecular biomarker and a neutralization of a virus causing food poisoning.

BACKGROUND

Currently, there are no known cells for allowing the culturing of Norovirus, and the use of chimpanzees as a Norovirus infection model (Karin Bok et al., Chimpanzees as an animal model for Human Norovirus infection and vaccine development. PNAS. 108(1): 325-330. 2011) is known. However, the use of chimpanzees requires a large space and high costs. Zebrafish (Danio rerio) may be used as an optimal animal model since the zebrafish exhibits high sensitivity to human infectious viruses, such as herpes simplex virus (Herpes simplex virus, Burgos, J. S et al., Zebrafish as a new model for herpes simplex virus type 1 infection. Zebrafish 5:323-333. 2008), hepatitis C virus (Cun-Bao Ding et al., Zebrafish as a potential model organism for drug test against hepatitis C virus, PLoS one. 8(6): e22921. 2011), and chikungunya virus (Chikungunya Virus, Nuno Palha et al., Real-time whole-body visualization of Chikungunya virus infection and host interferon response in zebrafish, PLoS pathog. 9:e1003619. 2013); the zebrafish can be subjected to experiments without relative difficulty; and the analysis of the full genome of the zebrafish has been completed.

In addition, proteomic analysis is useful in the confirmation of goal-oriented biomarkers through proteomic big data analysis. There were, until now, no reports about the attempt to analyze proteomic change through infection with Norovirus using zebrafish.

Throughout the entire specification, many papers and patent documents are referenced and their citations are represented. The disclosure of the cited papers and patent documents are entirely incorporated by reference into the present specification and the level of the technical field within which the present invention falls, and the details of the present invention are explained more clearly.

SUMMARY OF THE INVENTION

The present inventors endeavored to develop a method for detecting Norovirus, capable of distinguishing non-infectious Norovirus and infectious Norovirus from each other, and a natural plant derived material capable of neutralizing Norovirus, Hepatitis A Virus, and Rotavirus, which are enteric viruses causing food poisoning. As a result, the present inventors completed the present invention by providing a method for detecting infectious Norovirus using zebrafish (Danio rerio) and preparing a composition for neutralizing an enteric virus.

Accordingly, an aspect of the present invention is to provide a method for detecting Norovirus.

Another aspect of the present invention is to provide a method for screening an antiviral agent.

Still another aspect of the present invention is to provide a composition for neutralizing the infection with an enteric virus.

Other purposes and advantages of the present disclosure will become more obvious with the following detailed description of the invention, claims, and drawings.

In order to accomplish these objects, there is provided a method for detecting Norovirus using a Norovirus animal model, the method including:

(a) administering Norovirus to zebrafish (Danio rerio); and (b) detecting the expression level of a gene or protein selected from the group consisting of heat shock protein 90α (HSP90α), heat shock cognate 71 (HSC71), and transferrin receptor-1b (Tfr-1b), from the zebrafish in step (a).

The present inventors endeavored to develop a method for detecting Norovirus, capable of distinguishing non-infectious Norovirus and infectious Norovirus from each other, and a natural plant derived material capable of neutralizing Norovirus, Hepatitis A Virus, and Rotavirus, which are enteric viruses causing food poisoning. As a result, the present inventors provided a method for detecting infectious Norovirus using zebrafish (Danio rerio) and prepared a composition for neutralizing an enteric virus.

The method for detecting Norovirus of the present invention will be described in detail by steps.

Step (a): Administering Norovirus

First, Norovirus is administered into zebrafish (Danio rerio).

The Norovirus refers to the species Norwalk virus (genus Norovirus, family Caliciviridae).

The Norovirus is infectious Norovirus or non-infectious Norovirus.

The method for detecting Norovirus of the present invention can distinguish infectious Norovirus from non-infectious Norovirus. That is, the presence or absence of infectious Norovirus can be detected from a sample in which infectious Norovirus and non-infectious Norovirus are mixed.

The use of zebrafish is one of the main characteristics in the method for detecting Norovirus of the present invention.

Currently, there are no known cells for allowing the culturing of Norovirus, and the present invention, first, proposes a Norovirus infection model using zebrafish.

As used herein, the term "administering" refers to a method in which a dose of Norovirus is injected into zebrafish, and examples of the method include nasal, topical, systemic, inhalation, oral, intravenous, subcutaneous, intravascular, intraarterial, intratumoral, intraperitoneal, intraventricular, intra-granuloma, intranoral, intrarectal, intrapharyngeal, ocular, intraocular, or intramuscular injection.

Step (b): Detecting Expression Level of Gene or Protein

Next, the expression level of a gene or protein selected from the group consisting of HSP90α, HSC71, and Tfr-1 b is detected from the zebrafish in step (a).

The infectious Norovirus is detected through HSP90α, HSC71, and Tfr-1 b, which are zebrafish proteins overexpressed by Norovirus infection.

If the expression of a gene or protein selected from the group consisting of HSP90α, HSC71, and Tfr-1 b of the zebrafish infected with Norovirus is up-regulated, the zebrafish is determined as being infected with infectious Norovirus. On the contrary, if the expression of a gene or protein selected from the group consisting of HSP90α, HSC71, and Tfr-1 b is similar to that in a control (Norovirus non-infected group), the zebrafish is determined as being infected with non-infectious Norovirus.

As used herein to recite the gene or protein, the term "up-regulation" refers to a case in which the expression level of the gene or protein of a sample of investigation (for example, homogenized zebrafish tissue) is higher than the expression level of the gene or protein in the tissue that is not infected with Norovirus.

The up-regulation means an increase in the expression level by at least 1.1-fold, at least 1.3-fold, or at least 1.5-fold in determining Norovirus infection.

In the present invention, the detection of the expression level of the gene or protein may be carried out by various methods known in the art.

According to an embodiment of the present invention, step (b) is carried out by a genetic amplification reaction or an antigen-antibody reaction.

According to another embodiment of the present invention, step (b) is carried out by an antigen-antibody reaction. In this case, step (b) is carried out by using an antibody or aptamer specifically binding to a protein selected from the group consisting of HSP90α, HSC71, and Tfr-1b. As used herein, the term "antibody" refers to a specific protein molecule that is directed to an antigenic site. As for the purpose of the present invention, the antibody refers to an antibody specifically binding to the marker (the protein selected from the group consisting of HSP90α, HSC71, and Tfr-1b) or constituent proteins of the marker, and includes all of polyclonal antibodies, monoclonal antibodies, and recombinant antibodies. The antigen-antibody reaction manner has the same meaning as the immunoassay manner.

The polyclonal antibodies can be produced by the method known in the art, by which an antigen of the marker protein is injected into an animal and the blood is collected from the animal, thereby obtaining antibodies containing serum. These polyclonal antibodies can be prepared from a host of any animal species, such as a goat, a rabbit, a sheep, a monkey, a horse, a pig, a cow, or a dog.

The monoclonal antibodies may be produced by using a hybridoma method (Kohler and Milstein, European Journal of Immunology 6:511-519, 1976) or a phage antibody library (Clackson et al. Nature, 352:624-628, 1991; Marks et al. J. Mol. Biol., 222:58, 581-597, 1991), which is widely known in the art.

The antibodies produced by the method may be separated and purified by using a method, such as gel electrophoresis, dialysis, salt precipitation, ion exchange chromatography, or affinity chromatography. In addition, the antibody of the present invention includes functional fragments of an antibody molecule as well as an intact antibody having two full-length light chains and two full-length heavy chains. The functional fragments of the antibody molecule means a fragment retaining at least an antigen-binding function, and includes Fab, F(ab'), F(ab')2, and Fv fragments.

When the method of the present invention is performed using the antibody or aptamer, the present invention is performed according to a normal immunoassay method and thus may be used in detecting Norovirus.

This immunoassay may be carried out by various quantitative or qualitative immunoassay methods that have been developed in the conventional art and thus may be used in the detection of Norovirus. The immunoassay format includes western blot, enzyme linked immunosorbent assay (ELISA), capture-ELISA, radioimmunoassay (RIA), radioimmunodiffusion, ouchterlony immuno diffusion, rocket immunoelectrophoresis, tissue immunostaining, immunoprecipitation assay, complement fixation assay, fluorescence activated cell sorter (FACS), and protein chip, but the assay method of the present invention is not limited thereto. The immunoassay or immunostaining method is disclosed in Enzyme Immunoassay, E. T. Maggio, ed., CRC Press, Boca Raton, Fla., 1980; Gaastra, W., Enzymelinked immunosorbent assay (ELISA), in Methods in Molecular Biology, Vol. 1, Walker, J. M. ed., Humana Press, NJ, 1984; and Ed Harlow and David Lane, Using Antibodies: A Laboratory Manual, Cold Spring Harbor Laboratory Press, 1999, the entire contents of which are incorporated herein by reference.

The step of detecting the expression level of the gene or protein is carried out on one of day 1 to 5 after zebrafish is infected with Norovirus.

According to an embodiment of the present invention, the step is carried out on one of days 2 to 4 after the Norovirus infection.

According to another embodiment of the present invention, the step is carried out on day 3 after the Norovirus infection.

In accordance with another aspect of the present invention, there is provided a method for screening an antiviral agent against Norovirus using a Norovirus animal model, the method including:

(a) administering Norovirus to zebrafish (*Danio rerio*);

(b) administering an antiviral agent candidate against Norovirus to the zebrafish in step (a); and (c) detecting the expression level of a gene or protein selected from the group consisting of heat shock protein 90α (HSP90α), heat shock cognate 71 (HSC71), and transferrin receptor-1b (Tfr-1b), from the zebrafish in step (a), to determine efficacy of the antiviral agent candidate.

Since the method for screening an antiviral agent employs the method for detecting Norovirus, descriptions of overlapping contents between the two methods will be omitted to avoid excessive complication of the specification.

Step (a): Administering Norovirus

First, Norovirus is administered to zebrafish. Step (a) is the same as the above-described step (a) in the method for detecting Norovirus.

Step (b): Administering Antiviral Agent Candidate

Next, an antiviral agent candidate against Norovirus is administered to the zebrafish in step (a).

Examples of the antiviral agent candidate include low-molecular weight compounds, high-molecular weight compounds, nucleic acid molecules (e.g., DNA, RNA, PNA, and aptamer), proteins, sugars, lipids, and the like, but are not limited thereto.

Step (c): Determining Efficacy of Antiviral Agent Candidate

Next, the efficacy of the antiviral agent candidate is determined by detecting the expression level of a gene or protein selected from the group consisting of HSP90α, HSC71, and Tfr-1b from the zebrafish in step (b).

If the expression of a gene or protein selected from the group consisting of HSP90α, HSC71, and Tfr-1b is down-regulated by administering the antiviral agent candidate to the zebrafish in step (a), the antiviral agent candidate is determined as having an antiviral effect on Norovirus.

As used herein to recite the gene or protein, the term "down-regulation" refers to a case in which the expression level of the gene or protein in a sample of investigation (for example, homogenized zebrafish tissue) is lower than the expression level of the gene or protein in the tissue that is not infected with Norovirus. The down-regulation refers to a decrease in the expression level by at least 1.1-fold, at least 1.3-fold, or at least 1.5-fold in determining the antiviral agent candidate against Norovirus.

In accordance with still another aspect of the present invention, there is provided a composition for neutralizing the infection with an enteric virus, the composition containing concanavalin A (Con A) as an active ingredient.

As used herein, the term "neutralization" refers to an event in which an antiviral material (e.g., concanavalin A) binds to a biological activity site of a virus or a product thereof, thereby inhibiting the viral infection of cells.

According to an embodiment of the present invention, the enteric virus is Norovirus, Hepatitis A virus (HAV), or Rotavirus.

The concanavalin A binds to Norovirus.

According to an embodiment of the present invention, the concanavalin A has a $K_D$ value of $3.75 \times 10^{-7}$ M with respect to Norovirus.

The concanavalin A binds to Norovirus to neutralize Norovirus.

According to an embodiment of the present invention, the concanavalin A neutralizes Norovirus to 70-100%.

The concanavalin A of the present invention inhibits the expression of Tfr-1b protein of zebrafish against the Norovirus infection.

According to an embodiment of the present invention, the concanavalin A inhibits the expression of transferrin receptor-1b (Tfr-1b) of zebrafish.

The concanavalin A binds to Hepatitis A virus.

According to an embodiment of the present invention, the concanavalin A binds between viral protein 1 (VP1) domain and VP2 domain of Hepatitis A virus.

The binding between the concanavalin A and the Hepatitis A virus has a $K_D$ value of $1.28 \times 10^{-6}$ M.

The concanavalin A binds to Hepatitis A virus to neutralize Hepatitis A virus.

According to an embodiment of the present invention, the concanavalin A neutralizes Hepatitis A virus to 80-100%.

The concanavalin A binds to Rotavirus to neutralize Rotavirus.

According to an embodiment of the present invention, the concanavalin A neutralizes Rotavirus to 60-90%.

Features and advantages of the present invention are summarized as follows:

(a) The present invention provides a method for detecting Norovirus using a Norovirus animal model, and a method for screening an antiviral agent against Norovirus.

(b) The method for detecting Norovirus of the present invention can distinguish between infectious Norovirus and non-infectious Norovirus.

(c) The present invention provides a composition for neutralizing the infection with an enteric virus, the composition containing concanavalin A as an active ingredient.

(d) The composition of the present invention can neutralize viruses causing food poisoning.

BRIEF DESCRIPTION OF THE DRAWINGS

The above and other objects, features, and advantages of the present invention will be more apparent from the following detailed description taken in conjunction with the accompanying drawings, in which.

DETAILED DESCRIPTION

Hereinafter, the present invention will be described in detail with reference to examples. These examples are only for illustrating the present invention more specifically, and it will be apparent to those skilled in the art that the scope of the present invention is not limited by these examples.

Example 1: Confirmation of Norovirus Through PCR

Human infectious Norovirus (genotype GII-4) was heated at temperatures of 50 to 90° C. for 10 minutes, and then RNA was obtained. RNA isolation was conducted by using TRIzol (Invitrogen) according to the general RNA preparation protocol (Chomczynski P, Mackey K. Short technical report. Modification of the TRIzol reagent procedure for isolation of RNA from Polysaccharide- and proteoglycan-rich sources. Biotechniques 19(6): 942-945. 1995). 700 µl of Trizol was placed in 1.5 ml tubes, followed by light vortexing, and then 200 µl of chloroform was dispensed in each tube, followed by vortexing, and then each tube was allowed to stand for 5 minutes. After centrifugation at 12,000×g for 15 minutes at 4° C., the supernatant was transferred into new 1.5 ml tubes, and an equal volume of isopropanol was dispensed for each tube, followed by vortexing, and then each tube was allowed to stand for 10 minutes. After centrifugation at 12,000×g for 10 minutes at 4° C., the supernatant was removed, and 500 µl of 75% ethanol was dispensed, followed by light vortexing. After centrifugation at 7,500×g for 5 minutes at 4° C., the supernatant was removed, and RNA was obtained by using 10 µl of RNase-free water. To 10 µl of the obtained RNA, 1 µl of random primer, 4 µl of 5×M_MLV RTase buffer, 2 µl of 5×DTT, 2 µl of dNTP, 0.5 µl of RNase inhibitor, and 1 µl of M_MLV RTase were dispensed, followed by reaction at 65° C. for 10 minutes, at 37° C. for 1 hour, and at 72° C. for 5 minutes. RT-PCR was conducted by reaction of PCR premix (Bioneer), 16 µl of DNase-free water, and 2 µl of cDNA, which was synthesized by adding forward and reverse primers of 1 µl for each. PCR conditions were: 95° C. for 5 minutes, 40 cycles of 95° C. for 30 seconds, 55° C. for 30 seconds, and 72° C. for 45 seconds, and 72° C. for 5 minutes for last extension.

Figure 1:
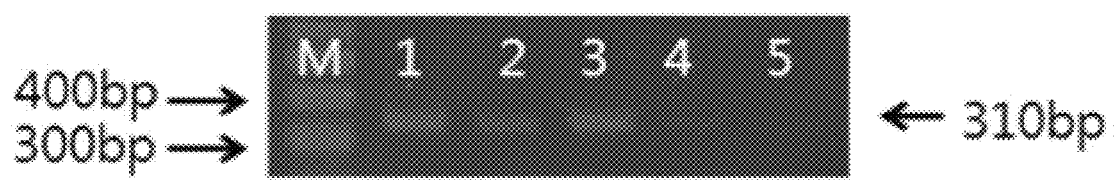
FIG. 1 shows results of confirming distinguishability between infectious Norovirus and non-infectious Norovirus through a gene amplification reaction.

As can be confirmed in FIG. 1, the electrophoresis results obtained by conducting RT-PCR of Norovirus heated at different temperatures of 50-90° C. also confirmed gene products in the heated non-infectious Norovirus. Therefore, it was confirmed that the infectious Norovirus and non-infectious Norovirus could not be distinguished by gene amplification.

Example 2: Selection of Biomarker Candidate of Infectious Norovirus

Zebrafish (*Danio rerio*) were purchased from a local aquarium, and five zebrafish were placed in each 1 L water bath using a reverse osmosis (RO) system water for an acclimation period of time. 400 mg of Tricaine (ethyl 3-aminobenzoate methanesulfonate salt, Sigma) reagent used in the fish anesthesia, and 2.1 ml of 1 M Tris were dissolved in 97.9 ml of distilled water, followed by adjustment to pH 7, thereby preparing an anesthesia solution. 4.2 ml of the anesthesia solution was dissolved in 100 ml of RO system water, and the fish were anesthetized. The previously prepared sterile phosphate buffer saline (PBS) and Norovirus (genotype G II-4) diluted in sterile PBS of 20 µl for each (titer $1\times10^6$ copy number) were intraperitoneally administered to the zebrafish. A lysis buffer (10 mM tris, 2 mM EDTA, 150 mM NaCl, 10% Triton X-100 10%, 10% NP40) was prepared, and a proteinase inhibitor and a phosphate were added to the lysis buffer at concentration ratios of 1:200 and 1:100, respectively. The mixture was dispensed into each 1.5 ml tube, and the zebrafish were rapidly frozen in liquefied nitrogen and then placed in the prepared 1.5 ml tubes. The zebrafish were cut into small tissues using sterile dissection scissors, and then homogenized using a homogenizer. These works were conducted in ice. The homogenized zebra tissues were subjected to vortexing once for every five minutes, followed by reaction in ice for 20 minutes. Thereafter, the centrifugation was conducted at 15,000 rpm for 13 minutes at 4° C., thereby obtaining supernatant. The zebrafish were sampled by date, and proteins were extracted. The protein change was confirmed by Coomassie Brilliant Blue. The protein change was confirmed using proteomic analysis in the zebrafish on day 3 on which there was the most significant difference.

Figure 2:
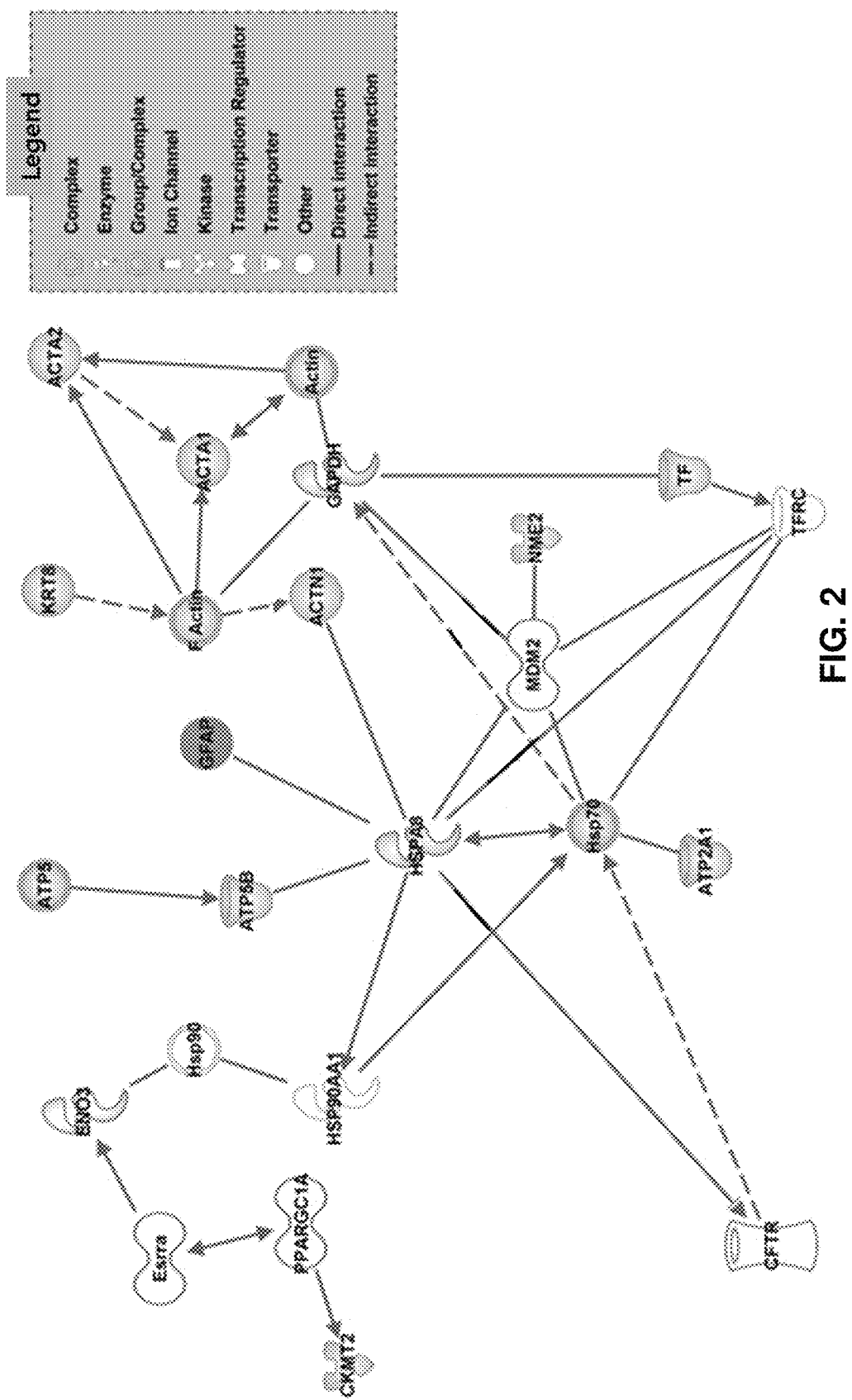
FIG. 2 is a diagram showing a protein change using ingenuity pathway analysis (IPA) on the basis of proteins analyzed through proteomic analysis.

As can be confirmed in FIG. 2 showing the protein change using the ingenuity pathway analysis (IPA) on the basis of the analyzed proteins, several important factors in the proteins were confirmed through protein analysis. Of these, three kinds of biomarkers, heat shock protein 90α (HSP90α), heat shock cognate 71 (HSC71), and transferrin receptor (Tfr) were confirmed to be overexpressed by infectious Norovirus.

Example 3: Confirmation on Biomarker Candidates of Infectious Norovirus

Biomarkers were specified according to the results of FIG. 2 showing the protein change analyzed by obtaining proteins of the zebrafish infected with human infectious Norovirus. 30 fig of each zebrafish protein was loaded on SDS-gel, and then the protein was transferred to the PVDF membrane (Immobilon-P, Millipore). Each membrane was blocked with TBST (1% Tween20 TBS) mixed with 5% skim milk for 1 hour. Each primary antibody of HSC71 (anti-HSC71 antibody, rabbit, Cell Signaling), HSP90α (anti-HSP90α antibody, rabbit, Anaspec), and Tfr-1b (anti-Tfr-1b antibody, rabbit, Anaspec) was dispensed at a concentration of 1:1000 in TBST mixed with 5% skim milk, followed by reaction overnight in a refrigerator. After washing three times with TBST for 10 minutes, secondary antibody (Polyclonal Goat, anti-rabbit immunoglobulins HRP, Dako) was dispensed at a concentration 1:2000 in TBST mixed with 5% skim milk, followed by reaction at room temperature for 2 hours. After washing five times with TBST for 5 minutes, the protein change was confirmed through a reaction with a western blot substrate (Luminata Crescendo, Millipore).

Figure 3:
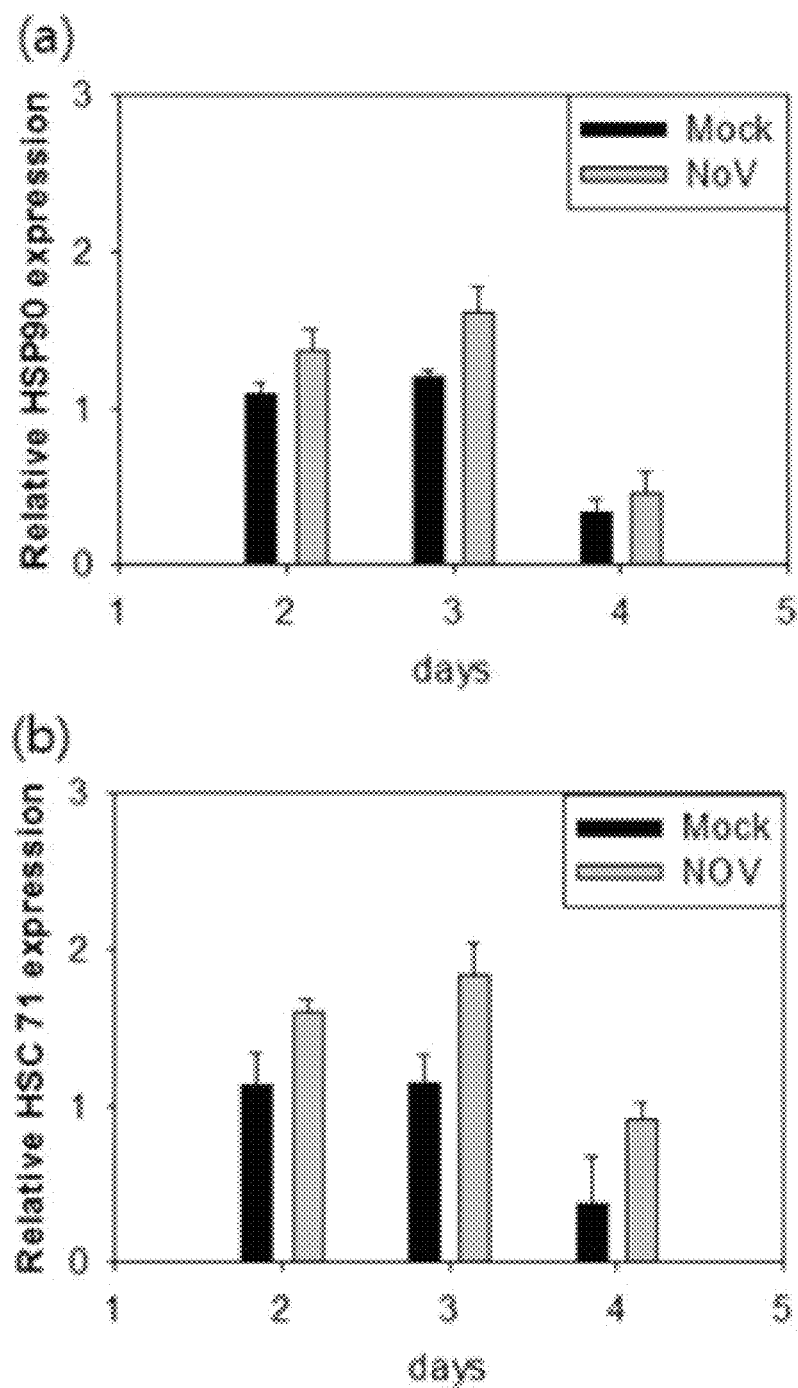
FIG. 3 shows results of confirming the expression change of heat shock protein 90α (HSP90α) and heat shock cognate 71 (HSC71) in zebrafish (Danio rerio) infected with infectious Norovirus, through western blot.
Figure 4:
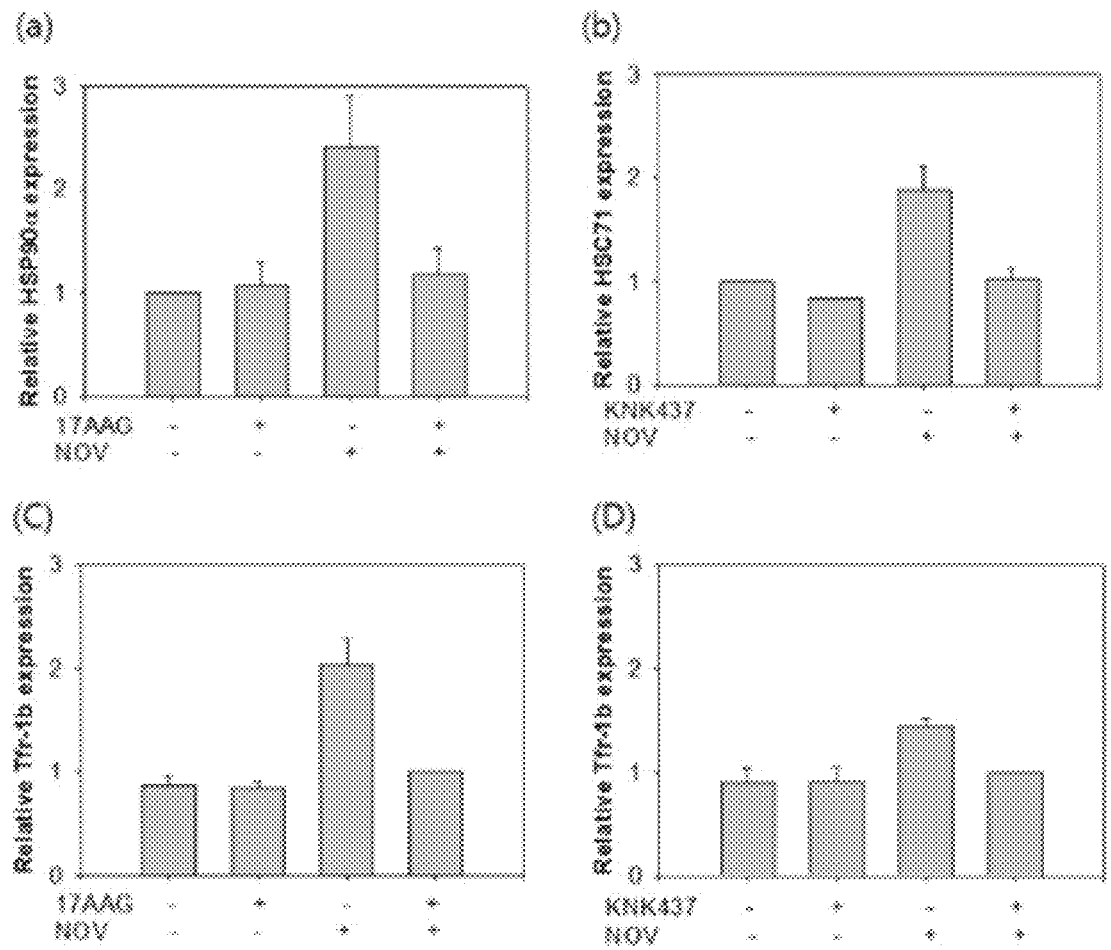
FIG. 4 shows results of confirming the possibility of HSP90α, HSC71, and Tfr-1 b as biomarkers by treatment with HSP090α inhibitor (17AAG) and HSC71 inhibitor (KNK437)
Figure 5:
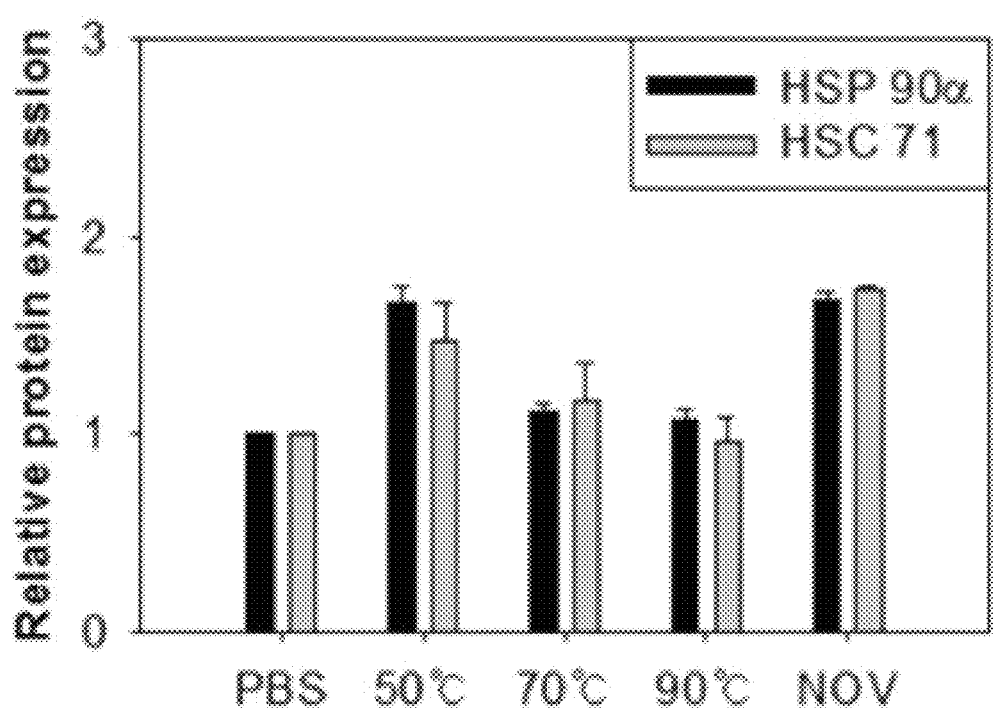
FIG. 5 shows results of confirming the expression changes of HSP90α and HSC71 in zebrafish infected with non-infectious Norovirus, through western blot.

FIGS. 3a and 3b show the results of confirming the expression of biomarkers, HSP90α and HSC71, by date through western blot. On day 3 of the infection, the protein expression between Mock (sterile PBS inoculation group) and Norovirus infection group were greatly differentiated, and on day 4 of the infection, the expression level was significantly reduced in both of the Mock group and the Norovirus infection group, and thus the effect could not be confirmed. Therefore, it was investigated the possibility as biomarkers of HSP90α and HSC71 by using inhibitors of HSP90α and HSC71, which are considered to be biomarkers, in the zebrafish proteins on day 3 of the Norovirus infection. FIGS. 4a and 4b show the results of reducing the protein expression, which was increased due to the Norovirus infection, through HSP90α inhibitor (17AAG, Sigma) and HSC71 inhibitor (KNK437, Sigma), and thus confirmed the functions as biomarkers. In addition, when the Tfr-1 b (transferrin receptor 1 b and Anaspec) antibody was used, the proteins were expressed in the Norovirus infection group, and when using together with HSP90α inhibitor and HSC71 inhibitor, the protein expression was reduced, but the protein expression was still confirmed (FIGS. 4c and 4d).

Example 4: Confirmation on Norovirus Infection in Zebrafish

Norovirus was heated at different temperatures for 10 minutes, and thus zebrafish were infected with non-infectious state Norovirus. On day 3 of the infection, the proteins were extracted from the zebrafish, followed by western blot, thereby confirming the protein change. The expression levels of HSP90α and HSC71 were increased in the Norovirus heated at 50° C. and wild type (WT) Norovirus, but similar levels of proteins were expressed in the Norovirus heated at 70° C. and 90° C. and in the zebrafish inoculated with only sterile PBS. Therefore, HSP90α and HSC71 could be confirmed as biomarkers that can distinguish between human infectious and non-infectious Norovirus. In addition, the expression of Tfr-1 b occurred in only groups infected with Norovirus heated at 50° C. and WT Norovirus, and thus HSP90α and HSC71 could be confirmed as more accurate biomarkers.

Example 5: Norovirus Neutralization of Con A

The previously prepared sterile phosphate buffer saline (PBS) and Norovirus diluted in sterile PBS of 20 µl for each case were intraperitoneally administered to the zebrafish anesthetized using an anesthetic solution. In addition, 100 µg/ml Con A (concanavalin A, sigma) was allowed to react with human infectious Norovirus (genotype G II-4, titer $1\times10^6$ copy number, reaction in a rotator at room temperature for 1 hour), and 20 µl of the resultant material was intraperitoneally administered to zebrafish. Zebrafish proteins were obtained 3 days after the infection, followed by western blot.

Figure 6:
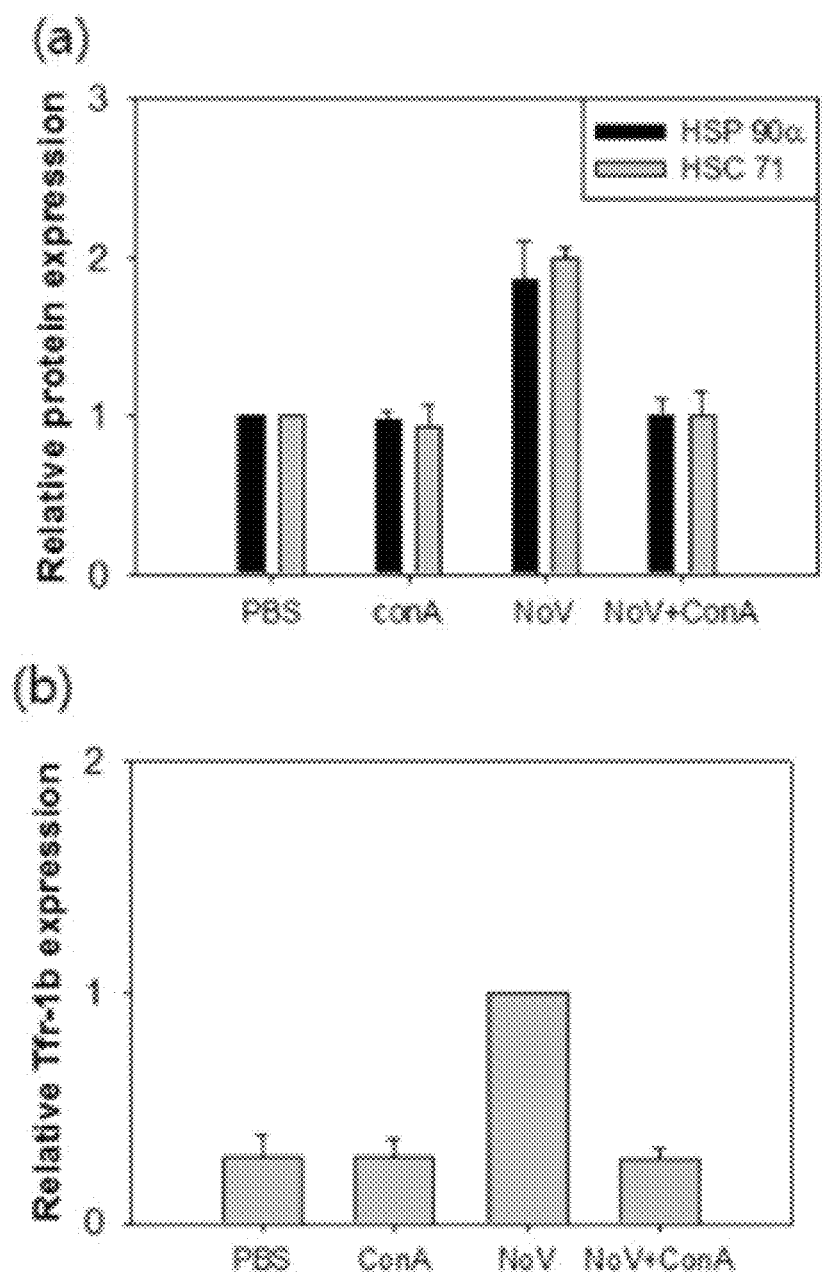
FIG. 6 shows results of confirming the expression changes of HSP90α, HSC71 and Tfr-1b in zebrafish administered with infectious viruses and Con A.

The expression levels of HSP90α and HSC71 were shown to still increase by about 2-fold in the group infected with only Norovirus (FIG. 6a). However, the proteins of the zebrafish infected with Norovirus plus Con A were expressed at similar levels compared with the group infected with only sterile PBS. In addition, as for Tfr-1b antibody, the zebrafish infected with Norovirus plus Con A showed a different tendency as compared with the treatment with inhibitors.

That is, the transferrin receptor was not expressed (FIG. 6b). This is thought to suppress the Norovirus infection per se.

Example 6: HAV and Con A Binding

The infection and culturing of Hepatitis A virus (HAV) occur in FRhk-4 cells (Rhesus monkey kidney, ATCC), and thus the FRhk-4 cells were utilized as a cell line capable of suppressing the infection mechanism. The FRhk-4 cells were cultured in a medium prepared by supplementing Dulbecco Modified Eagle Medium (DMEM, WELGENE) with 10% fetal bovine serum (FBS, WELGENE) and 1% penicillin streptomycin (Sigma). The FRhk-4 cells were dispensed in a 96-well plate at $8\times10^3$ cells/well, and after 24 hours, when the the cells reached about 80-90% of confluence, the virus inoculation was carried out. HAV was added at $1\times10^5$ unit/well, and an equal volume of HAV and 100 µg/ml Con A 100 were allowed to react each other, and the reaction material was dispensed to each well. RNA was obtained from the FRhk-4 cells treated with viruses by date, to investigate the copy number of HAV. RNA isolation was carried out by the method as in example 1.

Figure 7:
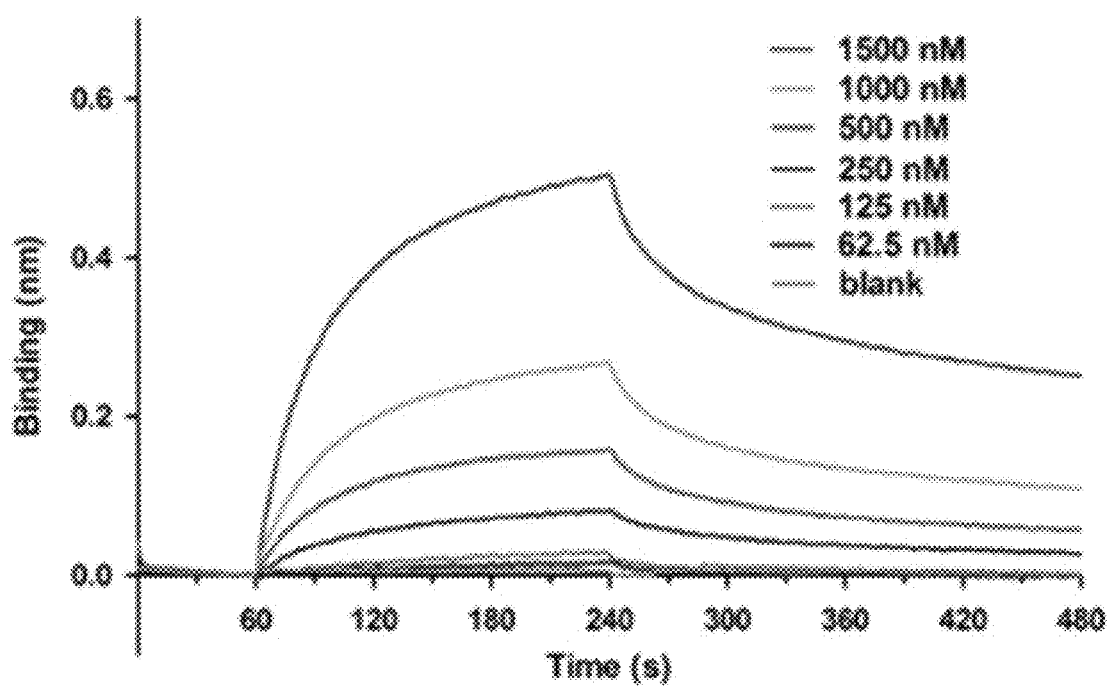
FIG. 7 shows results of confirming binding affinity by treating the Hepatitis A virus (HAV)-immobilized amine reactive 2nd generation biosensor (ARG2) chip with Con A.
Figure 8:
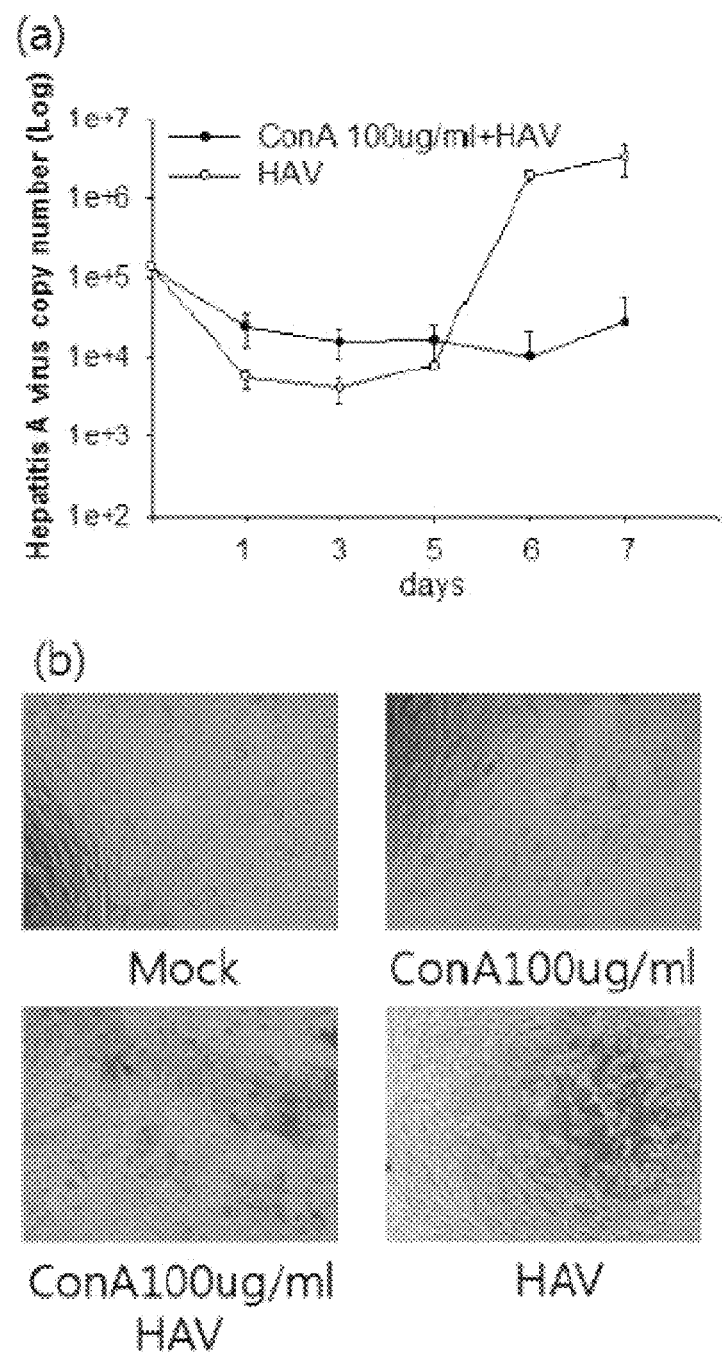
FIG. 8 shows results of confirming the suppression of Con A on HAV infection in Frhk-4 cells infected with HAV.

The binding affinity according to the concentration of Con A was investigated after HAV was immobilized to the ARG2 chip, and it was verified that the higher the Con A concentration, the more the Con A bound to the HAV-immobilized chip (FIG. 7). In the HAV infection group, the binding affinity was not largely changed until day 5 of infection, but on day 6 and day 7 of the infection, the binding affinity was increased by a value of about 2 log and the copies were $3.3\times10^6$ unit (FIGS. 8a and 8b). However, in the group infected with Con A plus HAV, the concentration of HAV was $2.7\times10^4$ unit, which corresponded to a lower level than the inoculation concentration. In addition, from the images, the cytopathic effect (CPE) was observed in the group treated with HAV, but the CPE was not observed in the group treated with HAV plus Con A. It is thought that Con A obstructs the intercellular penetration of HAV to suppress replication of HAV.

Figure 9:
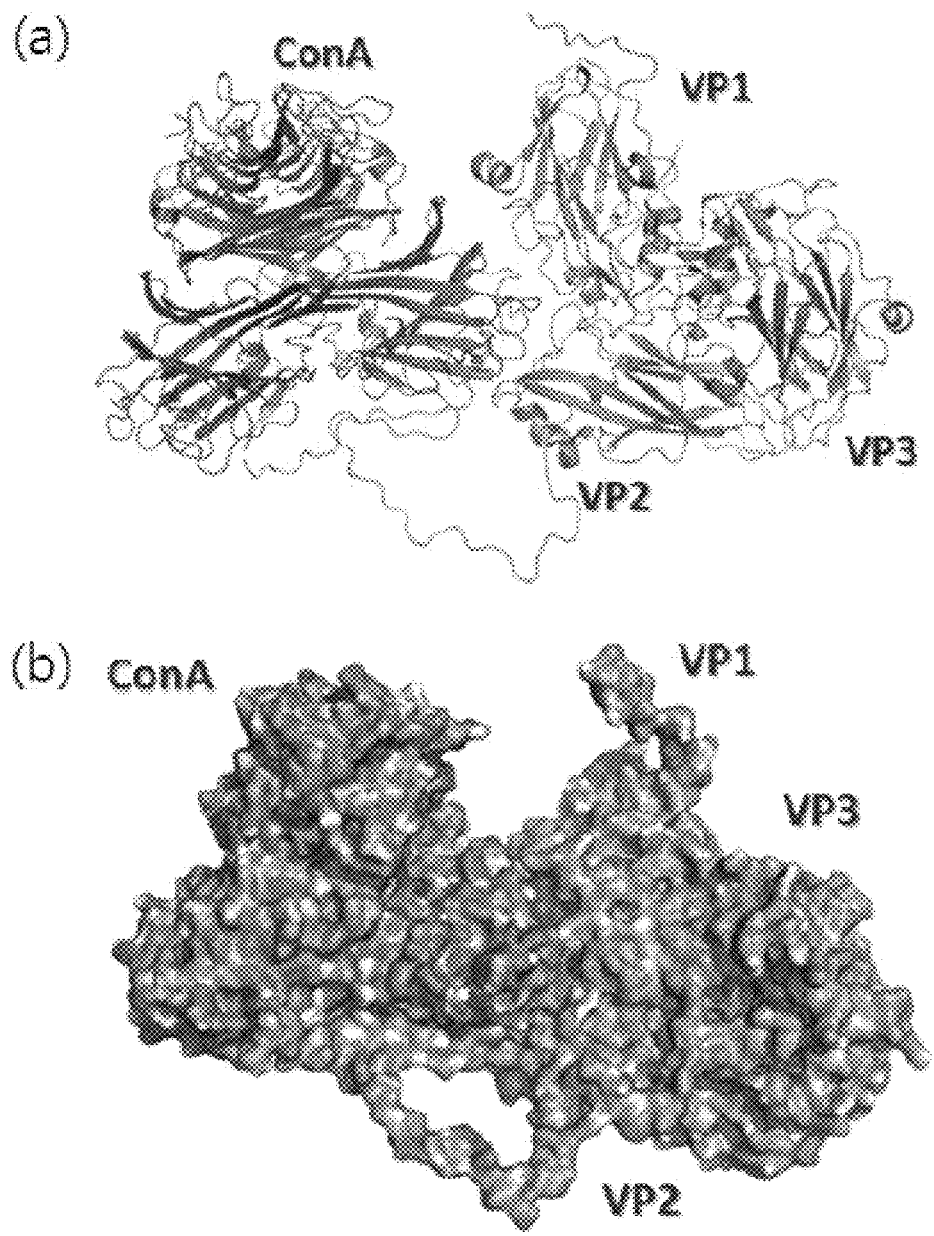
FIG. 9 shows the binding structure of Con A and HAV.

Con A is bound between HAV VP1 (structure forming protein) domain and HAV VP2 domain, and the N-terminus of the HAV VP2 domain binds with two molecules of Con A to stabilize the structure binding (FIG. 9).

Example 7: Norovirus and Con A Binding

It was investigated through RT-PCR and BioLayer interferometry (BLI) assay whether human infectious Norovirus and Con A bind to each other. RT-PCR was carried out according to the concentration of Norovirus to obtain the Ct value for each concentration of Norovirus. Each concentration of Norovirus was mixed with 100 µl of Con A-bound sepharose 4B resin (25 mg Con A/ml; C7275, Sigma), followed by reaction for 10 minutes. After the reaction, the resin was subjected to centrifugation (2000 g, 3 minutes, 4° C.) to remove the supernatant, and then the resin was washed three times with the PBS solution, followed by RT-PCR.

For the BLI assay, a BLItz system (ForteBio Inc., CA) was employed, and an amine reactive biosensor (ARG2) chip and a protein A chip were used. After the Norovirus was immobilized to the ARG2 chip, the binding was investigated at Con A concentrations of 0-10 µM. The test was carried out as follows: initial reference value, distilled water, 30 seconds: 20 mM 1-ethyl-3-(3-dimethylaminopropyl)-carbodiimide (EDC) and 10 mM sulfo-N-hydroxysuccinimide (s-NHS), 240 seconds; loading: Norovirus dissolved in NaOAc (pH 4), 360 seconds; blocking: 1 M ethanolamine (pH 8.5), 240 seconds; reference value: 10 mM PBS (pH 7.4), 60 seconds; association: Con A dissolved in PBS, 180 seconds; dissociation: 10 mM PBS (pH 7.4) 240 seconds. Sensorgrams are shown in FIGS. 10 and 11 using data analysis software 7.1.0.36 for the reference value (60 seconds), association (180 seconds), and dissociation (240 seconds).

Figure 12:
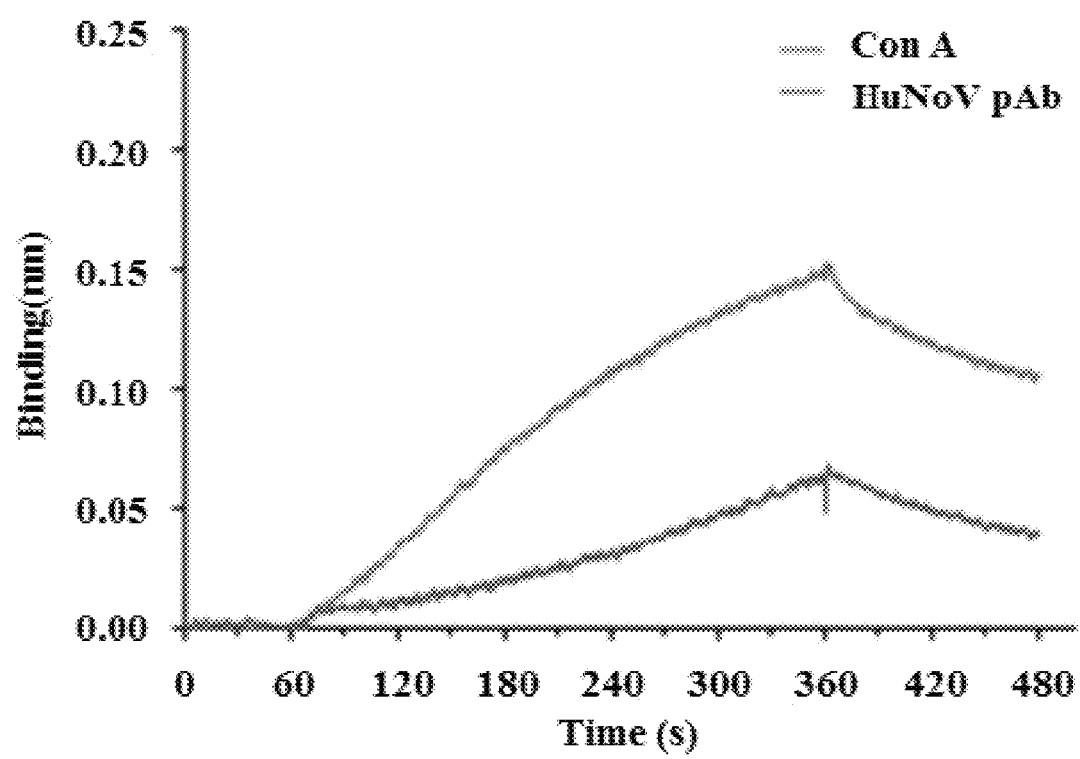
FIG. 12 shows results of confirming binding affinity of the antibody against Norovirus and Con A.

A competitive reaction test was carried out using the protein A chip in order to investigate whether the binding portions of the antibody against Norovirus and Con A with respect to Norovirus are the same as or different from each other. After the antibody was immobilized to the protein A chip, respective sensorgrams were investigated for samples of Con A, Norovirus, and Norovirus mixed with Con A (0.1 uM and 5 uM). The test on the protein A chip was carried out as follows: initial reference value: PBS, 30 seconds; loading: antibody dissolved in PBS, 120 seconds; reference value: 10 mM PBS (pH 7.4), 60 seconds; association: sample (FIG. 12) dissolved in PBS, 120 seconds; disassociation: 10 mM PBS (pH 7.4) 300 seconds. Sensorgrams are shown in FIG. 12 using data analysis software 7.1.0.36 for the baseline (60 seconds), association (120 seconds), and dissociation (300 seconds).

Figure 10:
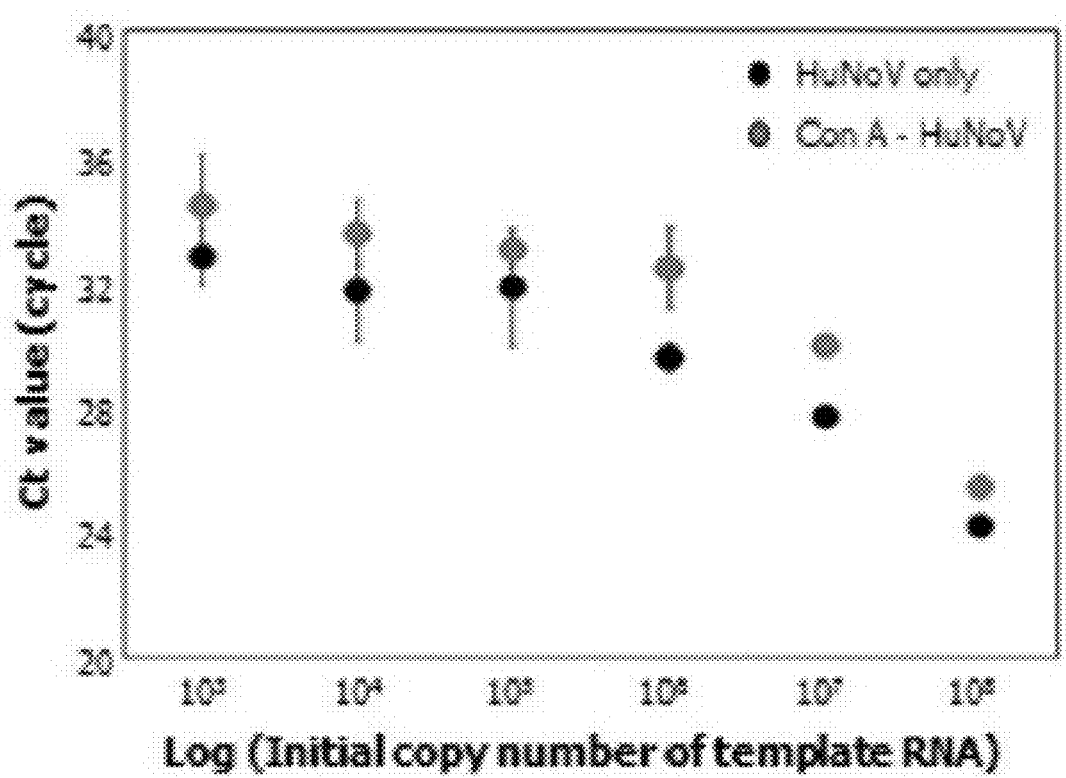
FIG. 10 shows results of confirming the binding between Con A and Norovirus through RT-PCR.

FIG. 10 shows the results of confirming the binding of Con A and Norovirus through RT-PCR. When Ct values for $1\times10^3$ to $1\times10^8$ copies/rat of Norovirus were compared with Ct values for Norovirus collected from Con A-bound sepharose 4B resin, the Ct value was reduced in a Norovirus concentration-dependent manner, and when Ct values of respective concentrations of Norovirus were compared with Ct values of Norovirus collected from Con A-bound sepharose 4B resin, the collection rate was confirmed to be 94.1% on average.

Figure 11:
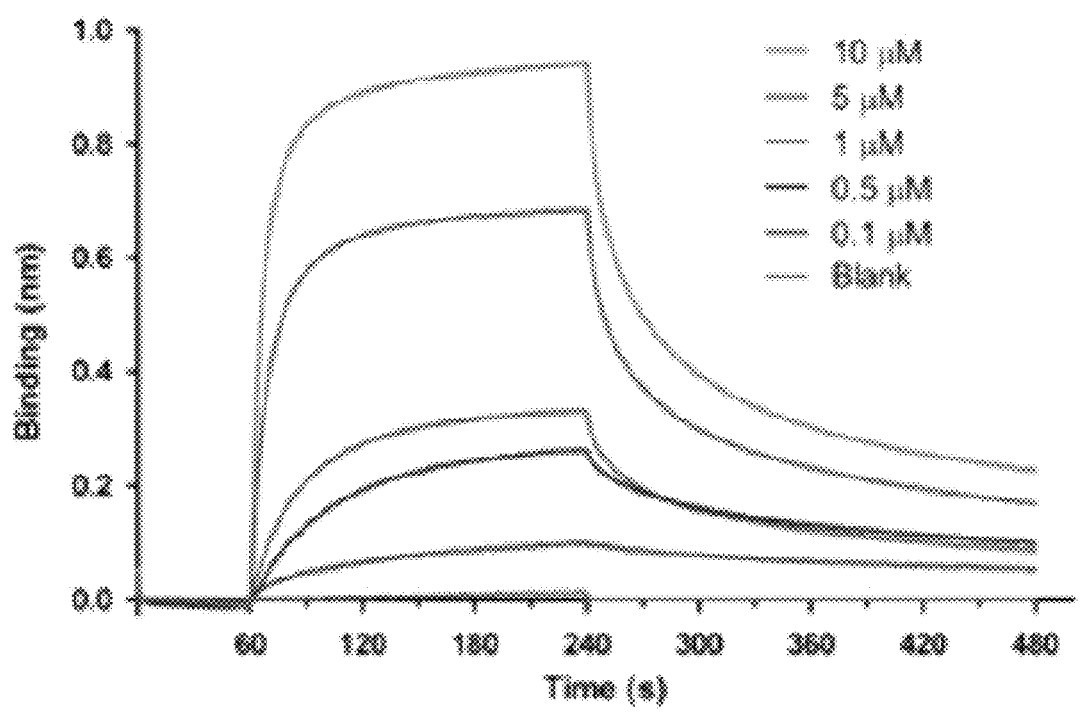
FIG. 11 shows results of confirming the binding affinity by treating Norovirus-immobilized ARG2 chip with Con A.

FIG. 11 shows the binding affinity according to the concentration of Con A after Norovirus was immobilized to the ARG2 chip, and it was verified that the higher the Con A concentration, the more the Norovirus bound to the Norovirus-immobilized chip. After the antibody and Con A were immobilized to ARG2 chips, respectively, the binding of Norovirus was investigated through the sensorgrams (FIG. 12). When sensorgrams of the antibody and Con A were compared with each other for the same concentration of Norovirus, it was verified that Con A bound to the Norovirus stronger than the antibody by 3-fold.

Figure 13:
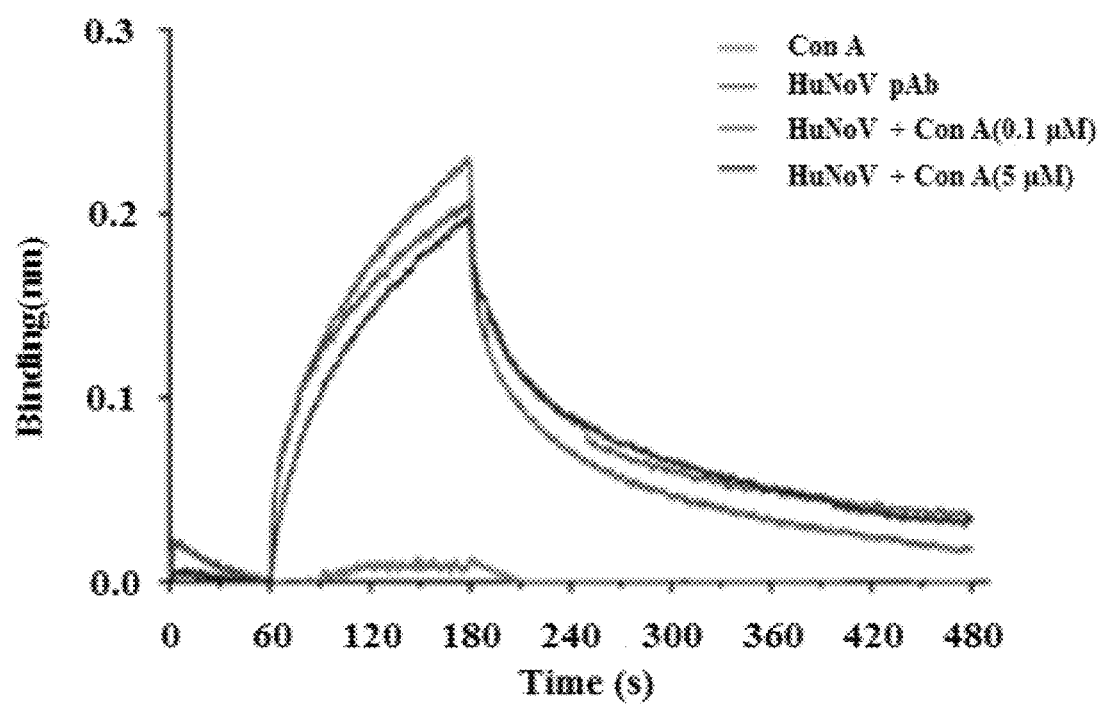
FIG. 13 shows results of comparing an epitope of the antibody against Norovirus and an epitope of Con A.

FIG. 13 shows the results through a competition test whether the binding portion between the antibody and Norovirus is the same as or different from the binding portion between Con A and Norovirus. After the Norovirus antibody was immobilized to the protein A chip, sensorgrams for Con A, Norovirus, and Norovirus plus Con A (0.1 μM and 5 μM) were compared with each other. As a result, it was verified that the Norovirus bound to the antibody-immobilized chip by 0.23 nm in the Norovirus sample as a positive control, and Con A did not bind to the antibody-immobilized chip in the Con A sample as a negative chip. Through these results, the sensorgrams for the binding with antibody in the Norovirus concentrations used in the test were obtained, and it could be verified that there was no binding between Con A and the antibody. Next, it was verified that the Norovirus bound to the antibody-immobilized chip by 0.2 nm in the respective samples of Norovirus and con A (0.1 μM and 5 μM), which were almost similar to sensorgrams in the positive control. In addition, the fact that the Norovirus was bound to the antibody-immobilized chip regardless of the binding of Con A and the Norovirus seems that the binding sites of Con A and the antibody with respect to the Norovirus were different from each other.

Example 8: Rotavirus and Con A Binding

In order to investigate whether Rotavirus among the poisoning viruses binds to Con A, a viral detection probe was manufactured by linking biotinylated Con A to streptavidin connected to magnetic beads as a magnetic body material. For the biotinylation of Con A, first, a labeling reaction was carried out by transferring 100 μl of Con A (1 mg/ml) into a reaction tube (component C). 1/10 of 1 M sodium bicarbonate was added, and mixed by pipetting, and then 1 μl of biotin-XX SSE was added and mixed, followed by reaction at room temperature for 15 minutes. Next, for the separation of Con A, the gel resin was allowed to fill an upper chamber, and 800 μl of resin was allowed fill a column, followed by centrifugation at 16,000 G for 15 seconds. The filling of resin was carried out using a centrifuge. After the resin was washed with PBS solution, the biotin-bound con A reaction material was placed in the spin column filled with the resin, followed by centrifugation at 16,000 G for 1 minute, thereby obtaining a reaction material. The thus reacted biotinylated Con A was linked to streptavidin-bound magnetic beads to manufacture a viral detection probe, and the manufacturing procedure thereof are as follows. Rotavirus was placed in the tube with the manufactured viral detection probe, followed by reaction at room temperature for 10 minutes. After the immunological reaction, the antigen-lectin binding portion was attached to magnets of the Con A-bound magnetic beads. The Con A-bound magnetic beads were washed three times with 200 μl of PBS to remove non-specifically bound impurities, and then floated in 100 μl of PBS, and the suspension was transferred to a new 1.5 ml tube to remove the supernatant. In order to separate streptavidin-bound antigen-Con A conjugate in the new tube, the conjugate was eluted with an eluent (50 mM glycine, pH 2.8), and neutralized to pH 7.5 with 100 mM Tris. In addition, RT-PCR was carried out for the pure separation of Rotavirus, and the virus was identified.

In order to investigate whether Rotavirus is detectable by immunoprecipitation using magnetic beads, RT-PCR of the eluted product was carried out to detect viruses. As Rotavirus primers used in the polymerase chain reaction (PCR) for the use of viral identification, RoV_VP4_F (5'-ATT TCG GAC CAT TTA TAA CC-3') and RoV_VP4_R (5'-TGG CTT CGC CAT TTT ATA GAC A-3') were used. The size of the PCR products amplified through the primers is 877 bp.

The RoV PCR conditions for viral identification were as follows. RoV PCR conditions: 35 cycles of denaturation at 94° C. for 30 seconds, annealing at 55° C. for 30 seconds, and elongation at 72° C. for 30 seconds, and the final elongation at 72° C. for 7 minutes. After RT-PCR, the PCR products were subjected to electrophoresis to monitor bands.

Figure 14:
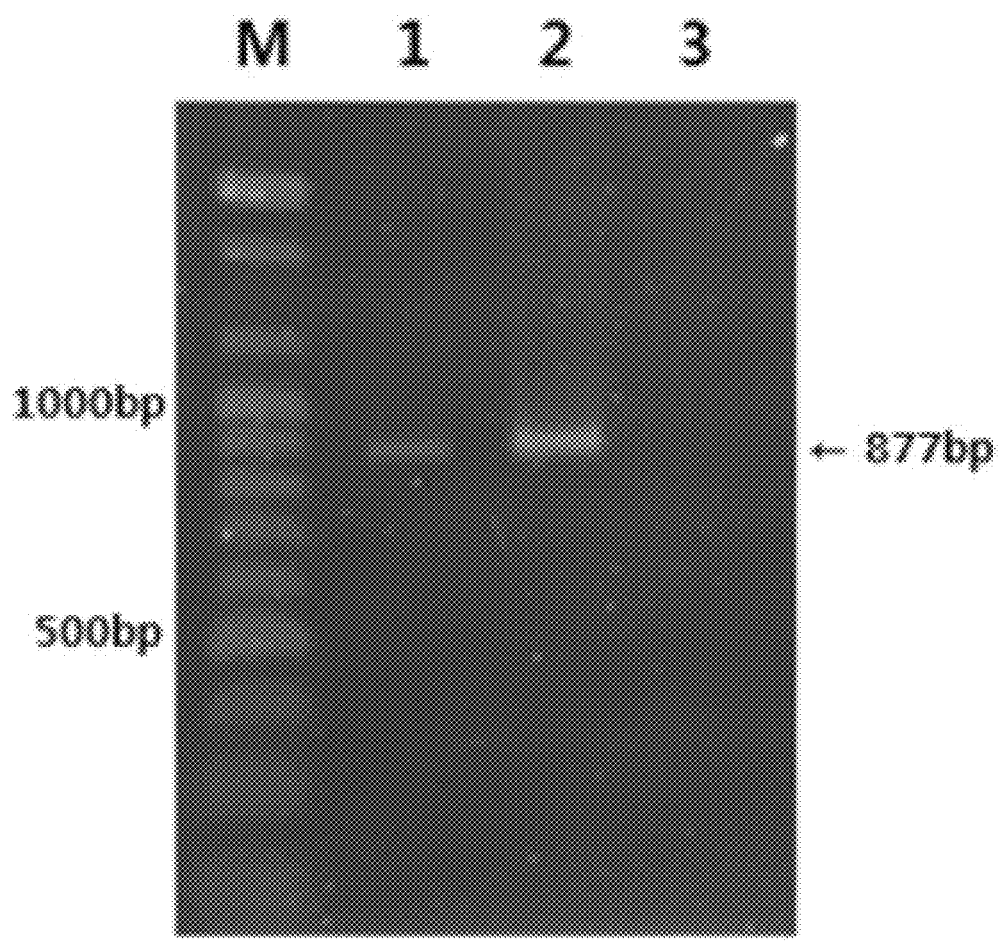
FIG. 14 shows results of confirming the binding of con A and Rotavirus.

FIG. 14 shows the results of electrophoresis after RT-PCR in order to investigate the binding of Con A and Rotavirus using the Con A-bound magnetic beads. Column 1 shows RT-PCR results of the solution obtained by performing elution on the magnetic beads, which were collected after the reaction with Rotavirus, using an eluent, and column 2 shows RT-PCR results of the Rotavirus stock solution. Column 3 shows a negative control for confirming the success or not of PCR. As a result, the band corresponding to Rotavirus amplification product of 877 bp was confirmed at the same position as in column 2 as a positive control. These results confirmed that Con A was bound to Rotavirus.

Example 9: Rotavirus and Con A Binding

The infection and culturing of Rotavirus occur in MA-104 cells (Green monkey kidney, ATCC), and thus the MA-104 cells were utilized as a cell line capable of suppressing the infection mechanism. The MA-104 cells were cultured in a medium prepared by supplementing Dulbecco Modified Eagle Medium (DMEM, WELGENE) with 10% fetal bovine serum (FBS, WELGENE) and 1% penicillin streptomycin (Sigma). The MA-104 cells were dispensed in a 96-well plate at $1 \times 10^4$ cells/well, and after 24 hours, when the the cells reached about 80-90% of confluence, the virus inoculation was carried out. Rotavirus was added at $1 \times 10^5$ unit/well, and an equal volume of Rotavirus and 100 μg/ml Con A 100 were allowed to react each other at room temperature for 1 hour, and the reaction material was dispensed to each well. RNA was obtained from the MA-104 cells treated with viruses by date, to investigate the copy number of Rotavirus. RNA isolation was carried out by the method as in example 1.

Figure 15:
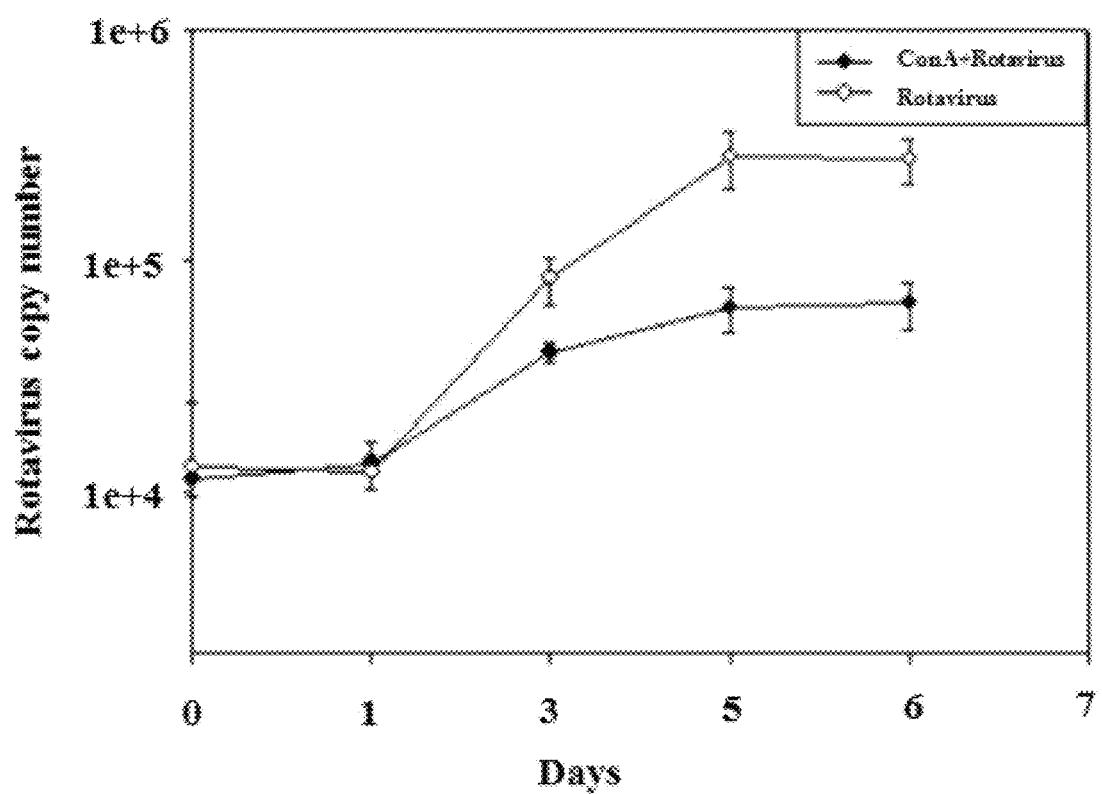
FIG. 15 shows results of Rotavirus neutralization by Con A.

In the Rotavirus infection group, the binding affinity was not largely changed until day 1 of infection, but on day 3 and day 5 of the infection, the binding affinity was increased by a value of about 1.5 log and the copies were $2.7 \times 10^5$ unit. However, in the group infected with Con A plus Rotavirus, the concentration of Rotavirus was $6.4 \times 10^4$ unit, which was reduced by a value of 1 log compared with the Rotavirus infection group. These results showed similar tendencies compared with the test using HAV plus Con A, indicating that the Con A neutralized Rotavirus to suppress the Rotavirus infection (FIG. 15).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for inhibiting gene expression of at least one selected from transferrin receptor-1b (Tfr-1b), heat shock protein 90α (HSP90α), and heat shock cognate 71 (HSC71) in a subject, comprising:
   administering to the subject an effective amount of a composition comprising concanavalin A (Con A),
   wherein Tfr-1b, HSP90α, and HSC71 expression levels are increased due to Norovirus infection.

2. The method of claim 1, wherein the concanavalin A ne

3. The method of claim 1, wherein the concanavalin A has a $K_D$ value of $3.75 \times 10^{-7}$ M with respect to Norovirus.

4. A method for neutralizing infectivity of Norovirus virions comprising administering to a subject in need thereof an effective amount of a composition comprising concanavalin A (Con A).

5. The method of claim 4, wherein the Norovirus virions are from the GII Norovirus genogroup.

6. The method of claim 4, wherein the concanavalin A neutralizes Norovirus infection by 70-100%.

7. The method of claim 4, wherein the concanavalin A has a KD value of 3.75×10-7 M with respect to Norovirus.

* * * * *